United States Patent [19]
Ko et al.

[11] Patent Number: 6,137,018
[45] Date of Patent: Oct. 24, 2000

[54] CHEMICAL REFINING METHOD AND REUSE SYSTEM FOR SEMICONDUCTOR DEVICE MANUFACTURING

[75] Inventors: Yong-kyun Ko; June-ing Gil; Sang-mun Chon, all of Kyungki-do, Rep. of Korea

[73] Assignee: Samsung Electronics Co., Ltd., Suwon, Rep. of Korea

[21] Appl. No.: 09/115,827

[22] Filed: Jul. 15, 1998

[30] Foreign Application Priority Data

Aug. 19, 1997 [KR] Rep. of Korea ............... 97-39311

[51] Int. Cl.[7] .................................................. C07C 29/74
[52] U.S. Cl. .......................................... 568/913; 568/916
[58] Field of Search .................................. 568/913, 916

[56] References Cited

U.S. PATENT DOCUMENTS 5,571,703  11/1996  Chieffalo et al. ................... 435/105
5,753,125   5/1998  Kreisler ............................. 210/710

*Primary Examiner*—Laura L. Stockton
*Attorney, Agent, or Firm*—Jones Volentine, LLC

[57] ABSTRACT

A chemical refining and reuse method and apparatus efficiently remove water from a waste chemical used in a semiconductor device fabrication process. The method is superior to conventional refining methods, in that water is removed at the end of the refining process, followed only by particle removal, so that water is not reintroduced into the waste chemical during metallic impurity removal. Therefore, the refined waste chemical has a percentage of water therein which is equal to that of the chemical in an initial raw state. The method includes: a) removing ionic impurities contained in the waste chemical; b) removing metallic impurities contained in the waste chemical after removing the ionic impurities; c) removing water contained in the waste chemical after removing the metallic impurities; and d) removing particles contained in the waste chemical after removing the water.

15 Claims, 3 Drawing Sheets

6,137,018

CHEMICAL REFINING METHOD AND REUSE SYSTEM FOR SEMICONDUCTOR DEVICE MANUFACTURING

BACKGROUND OF THE INVENTION

1. Field of the Invention

The present invention relates to a chemical refining method and reuse system for semiconductor device manufacturing, and more particularly, to a chemical refining method and reuse system wherein water is efficiently removed during refining of Isopropyl Alcohol (IPA).

2. Background of the Related Art

Generally, drying methods, such as Isopropyl Alcohol (IPA) evaporation drying or spin drying, are used to dry wet wafers after wet-cleaning processes are performed during semiconductor device fabrication.

In IPA evaporation drying, wafers pass through a cleaning process using deionized water and are then immersed for a specified time into a bath containing IPA. Any water remaining on the wafer surface becomes vaporized along with the high volatility IPA.

In spin drying, wafers pass through the cleaning process using deionized water and are then placed on a spin chuck and rotated with a constant RPM so as to remove any water remaining on the wafer surface. Afterwards, the wafers are moved to a hot plate in order to heat the wafers for further drying.

The IPA evaporation drying method is the more effective of the two methods, but IPA having a strong volatility and a high purity is required. As a result, manufacturing expenses are higher using the IPA evaporation method.

Therefore, a method for refining and reusing waste IPA from the IPA evaporation drying operation is used to reduce manufacturing expenses and to protect the environment by purifying the waste IPA for reuse. The purification must remove, from the waste IPA, ionic impurities, metallic impurities, water, particles and various kinds of contaminants used in the semiconductor device fabrication process. Among these contaminants, the amount of water in the waste IPA most greatly affects the volatility of IPA.

FIG. 1 is a schematic block diagram showing a conventional refining process for reusing waste Isopropyl Alcohol (IPA).

As shown in FIG. 1, IPA raw material is introduced into a cleaning tank or bath 14 from a supply source 10 through a supplying means 12. The IPA in the bath 14 is used for evaporation-drying wafers and is then discharged into a waste tank 16. The discharged waste IPA passes through an ion impurity removal part 18 for removing ionic impurities. Then, water is removed by repeatedly conducting a water removal process three times in water removal parts 20, 22, 24. After the water removal process, the IPA passes to a metallic impurity removal part 26 for removing metallic impurities. From there, the IPA passes through a filter 28 for removing any remaining particles and then, is stored in a storage tank 30. The stored IPA passes again through supplying means 12, and is reintroduced into the bath 14 so as to be reused in the wafer evaporation drying.

As can be seen in FIG. 2, which shows the water quantity of the waste IPA as it progresses through the above conventional process, the percentage of water contained in the IPA is reduced during the three repetitions of the water removal process and is then increased by the metallic impurity removal process. That is, the percentage of water contained in the IPA after the three water removal processes is about 0.01% but is increased to about 0.1% by the metallic impurity removal process. The increased percentage of water remains through the final steps, thereby resulting in a difference, by a factor of more than ten times the percentage of water contained therein, between the quality of the refined waste IPA compared with the initial IPA raw material. Other ionic impurities and metallic impurities, etc., in the refined waste IPA are decreased down to the level of the initial IPA raw materials by the respective removal processes.

On the other hand, the three steps of removing water from the waste IPA do not have the effect of returning the waste IPA to the purity level of the initial IPA raw materials. Therefore, it is difficult to obtain the desired purity level of IPA which can be reused and reintroduced in the semiconductor device fabrication process.

SUMMARY OF THE INVENTION

The present invention is directed to a chemical refining method and a purification system for reusing waste chemical by providing the efficient removal of water from the chemical, which substantially overcomes one or more of the problems due to the limitations and disadvantages of the related art.

One object of the present invention is to provide a chemical refining method and a purification system, wherein the amount of the water contained in the Isopropyl Alcohol (IPA) is reduced to the level of the initial raw material of IPA during the refining process of waste IPA.

To achieve these and other advantages and in accordance with the purpose of the present invention, as embodied and broadly described, the chemical refining method for reusing chemical used in the semiconductor device fabrication process includes: a) removing ionic impurities contained in the waste chemical; b) removing metallic impurities contained in the waste chemical after removing the ionic impurities; c) removing water contained in the waste chemical after removing the metallic impurities; and d) removing particles contained in the waste chemical after removing the water.

The chemical is Isopropyl Alcohol (IPA), and the step of removing ionic impurities is carried out by passing the waste chemical through charging material for ion removal.

In addition, the step of removing metallic impurities is carried out by heating and vaporizing the waste chemical, and collecting and cooling the vaporized waste chemical so as to separate the metallic impurities from the waste chemical. The metallic impurities removed in the step of removing the metallic impurities comprise sodium (Na), iron (Fe), aluminum (Al), copper (Cu) and calcium (Ca). In addition, water is removed by heating and vaporizing the waste chemical, collecting it and passing it through a filter through which only water passes, for water removal in the vacuum state, and collecting the waste chemical which does not pass through the filter. The water removal step is carried out a plurality times, and preferably, such that the percentage of water contained in the waste chemical is reduced to the percentage of water found in the initial raw chemical.

A purification system for reusing a waste chemical used in a semiconductor device fabrication process includes a processing part for carrying out the semiconductor device fabrication process using the chemical supplied from a chemical supply source. A waste tank stores the waste chemical used in the processing part. An ionic impurity removal part is connected to the waste tank for removing ionic impurities from the waste chemical. A metallic impurity removal part is connected to the ionic impurity removal part for removing metallic impurities from the waste chemical. A water removal part is connected to the metallic impurity removal part for removing water from the waste chemical. Finally, a particle removal part is connected to the water removal part for removing particles from the waste chemical. A storage tank stores the waste chemical which has passed through the particle removal part and supplies it for reuse in the processing part.

The water removal part is formed such that a plurality of water removal parts are connected in series, and preferably, at least three are installed. The particle removal part is formed with a polyethylene filter.

A plurality of storage tanks are connected in parallel to ensure a stable supply of the refined waste chemical, and the processing part comprises a cleaning tank into which wafers being processed are dipped.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings illustrate an embodiment of the invention, in which.

DETAILED DESCRIPTION OF PREFERRED EMBODIMENT

Reference will now be made in detail to a preferred embodiment of the present invention, an example of which is illustrated in the accompanying drawings.

Figure 1:
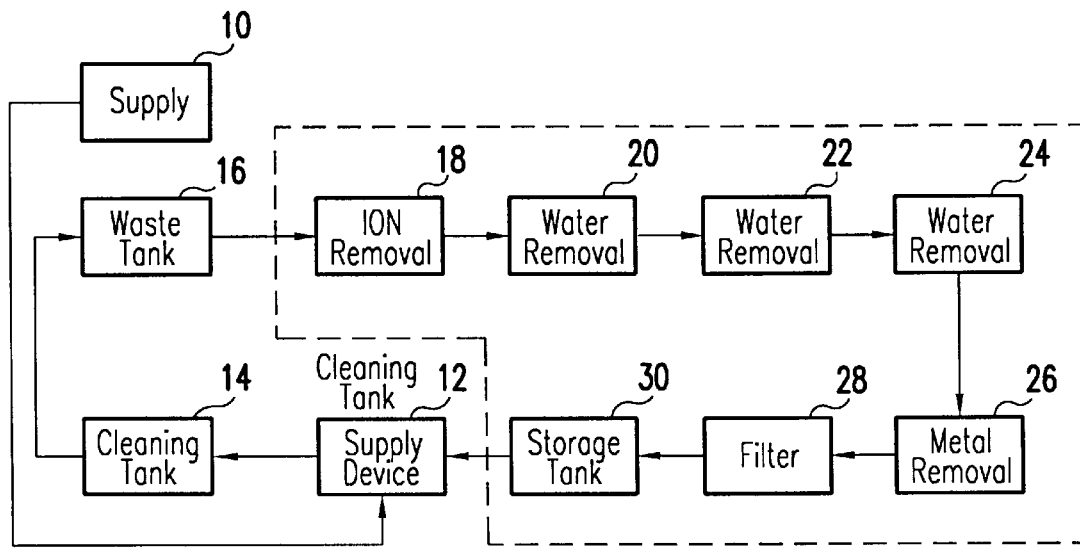
FIG. 1 is a schematic block diagram showing a conventional refining process for reusing waste Isopropyl Alcohol (IPA)
Figure 2:
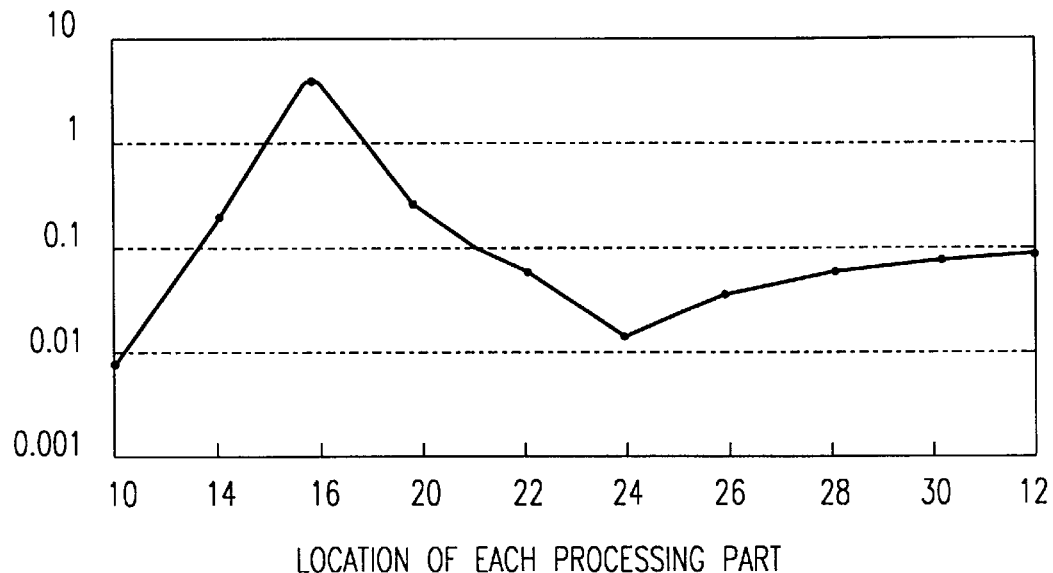
FIG. 2 is a graphical representation showing the percentage of water contained in the waste IPA at each of the processing positions shown in FIG. 1.
Figure 3:
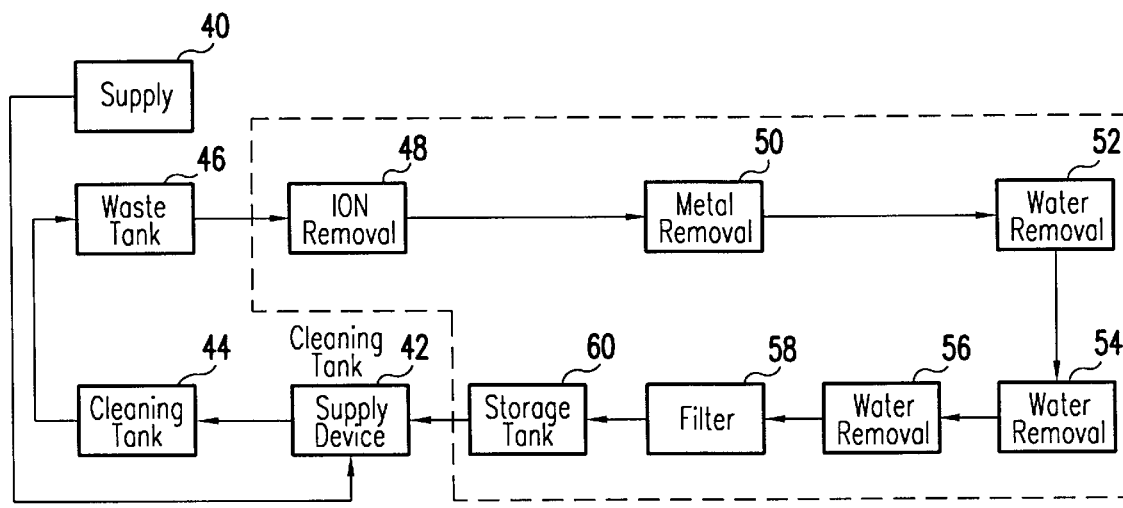
FIG. 3 is a schematic block diagram showing the refining process for reusing waste Isopropyl Alcohol (IPA) according to the present invention.

FIG. 3 is a schematic block diagram showing the refining process for reusing waste Isopropyl Alcohol (IPA) according to the present invention.

As shown in FIG. 3, IPA is supplied into a cleaning tank or bath 44 from its supply source 40 through a cleaning tank supplying device 42. Wafers to be cleaned are dipped into bath 44. When the wafers are removed from the bath, the IPA will vaporize so as to dry the wafers, and the used IPA is then discharged to a waste tank 46.

The refining process for reusing waste Isopropyl Alcohol (IPA) begins when the discharged waste IPA passes through an ionic impurity removal part 48 for removal of ionic impurities. Here, while charging material for ion removal passes through the IPA, (−) ions adsorb (+) ions, and (+) ions adsorb (−) ions so that the ionic impurities are removed.

Figure 5:
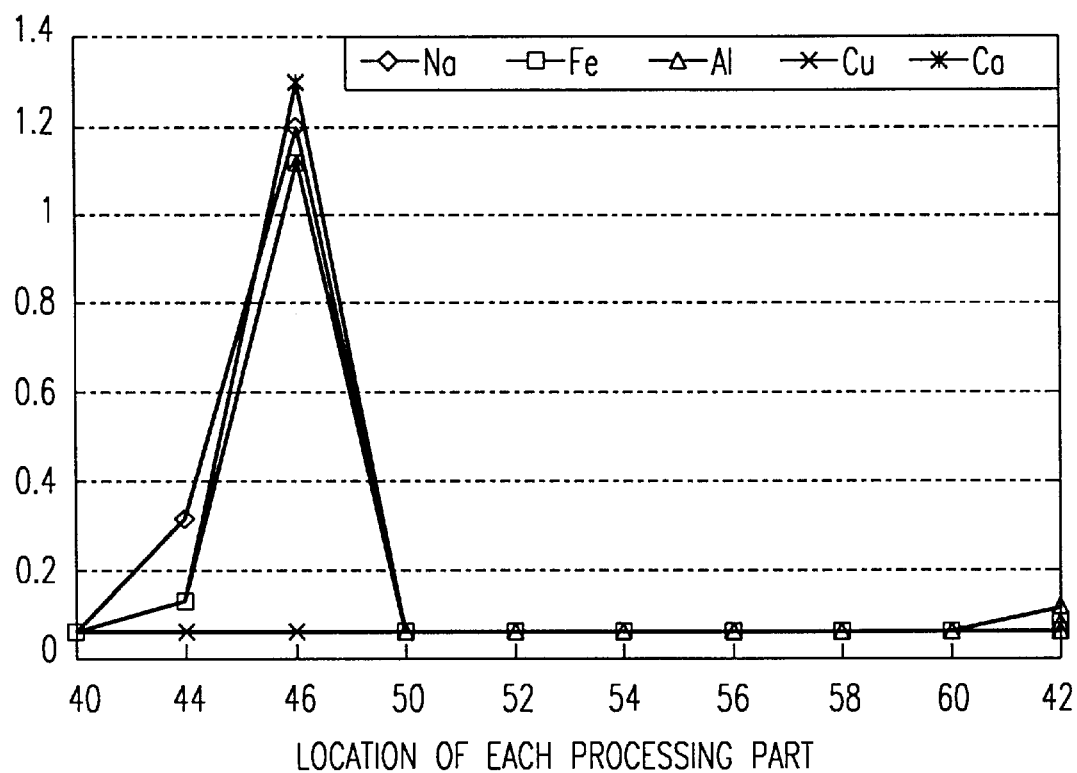
FIG. 5 is a graphical representation showing the quantity of metallic elements contained in the waste IPA at each of the processing positions shown in FIG. 3.

Then, the waste IPA passes to a metallic impurity removal part 50 in order to remove metallic impurities therein. Here, the IPA is heated to boiling at 82° C. in a container equipped with a hot plate, and the vaporized IPA, which is largely free of metallic elements, is collected and cooled. In FIG. 5, the level of metallic impurities in the waste IPA (parts per billion (ppb)) after the step of metallic impurity removal is the same as that of the initial IPA raw material.

The waste IPA then passes to water removal parts 52, 54, 56, which are connected in series. The waste IPA is subjected to the water removal operation three times, in which the IPA is heated to 110° C. in a vacuum state in a container equipped with a hot plate. The vaporized IPA and water are fed to a filter that only allows water to pass. The water passing through the filter is liquefied and removed by a vacuum pump. Here, the reason for the high heating temperature is that the temperature for evaporation is higher in the vacuum state than in the normal atmosphere. The vacuum level is 2 to 5 Torr.

The IPA which does not pass through the filter is collected and then passes through a particle removal part 58 made from 0.09 μm of polyethylene film in order to remove particles therein and is thereafter stored in a storage tank 60. The refined IPA stored in the storage tank 60 is supplied into the bath 44 through the cleaning tank supplying device 42. A plurality of storage tanks 60 can be installed in parallel in order to insure a stable supply of IPA.

Figure 4:
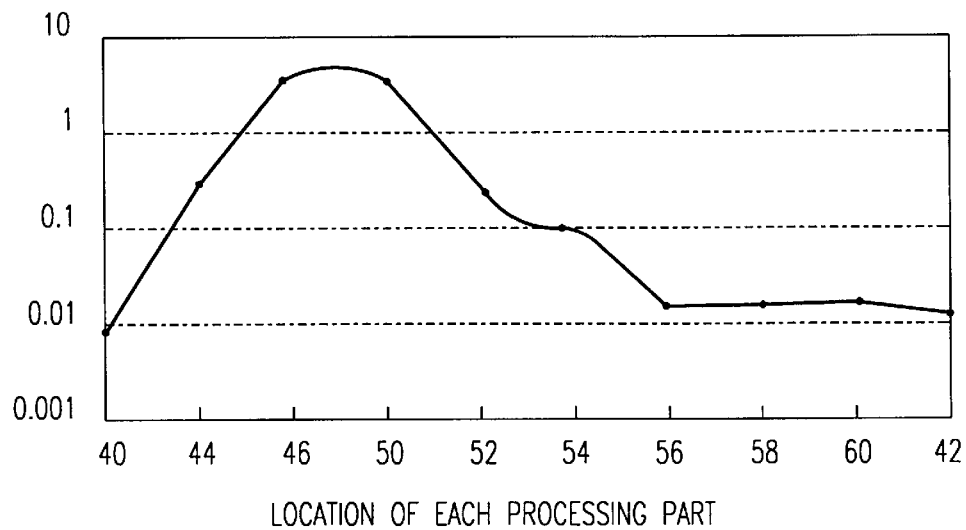
FIG. 4 is a graphical representation showing the percentage of water contained in the waste IPA at each of the processing positions shown in FIG. 3.

As described above, the waste IPA passes through several refining steps for removal of impurities, wherein an ionic impurity removal step, a metallic impurity removal step, water removal steps, and a particle removal step are performed, in that order. As a result, as shown in FIG. 4, the problem of the conventional art in which the quantity of water in the IPA increases during the metallic removal step (which takes place after the water removal step) is solved.

Note also that the quantity of water in the unrefined waste IPA initially discharged into the waste tank is 5% to 10%, which is quite large. On the other hand, the quantity of water in the refined IPA according to the present invention and stored into the storage tank is 0.01%, which is less than ⅛ of the quantity of water (0.09%) in the waste IPA refined according to the conventional refining process. In other words, the IPA refined by the process according to the present invention has a purity of 99.99% and is suitable for reuse.

It will be apparent to those skilled in the art that various modifications and variations of the present invention can be made without departing from the spirit or scope of the present invention. Therefore, it is intended that the present invention not be limited to the particular embodiment disclosed, but that the present invention include all embodiments falling within the scope of the appended claims.

What is claimed is:

1. A chemical refining method for refining and reusing a chemical used in a semiconductor device fabrication process, comprising:

collecting the chemical as waste chemical after it has been used in the fabrication process;

removing ionic impurities from said waste chemical;

removing metallic impurities from said waste chemical after removing said ionic impurities;

removing water from said waste chemical, after removing said metallic impurities, until the percentage of water in the waste chemical is at the same level as that of the chemical in a raw state before its use in the fabrication process;

removing particles from said waste chemical after removing said water; and subsequently returning the waste chemical to storage for use in the fabrication process;

wherein said chemical is Isopropyl Alcohol (IPA).

2. The chemical refining method as claimed in claim 1, wherein said removing ionic impurities comprises passing said waste chemical through charging material for ion removal.

3. The chemical refining method as claimed in claim 1, wherein said removing metallic impurities comprises heating and vaporizing said waste chemical, and collecting and cooling said vaporized waste chemical so as to separate said metallic impurities from said waste chemical.

4. The chemical refining method as claimed in claim 3, wherein said removing metallic impurities comprises removing Na, Fe, Al, Cu, and Ca.

5. The chemical refining method as claimed in claim 1, wherein said removing water is carried out in a vacuum state and comprises heating and vaporizing said waste chemical, passing said vaporized waste chemical through a filter through which only water passes, and collecting said waste chemical which does not pass through the filter.

6. The chemical refining method as claimed in claim 1, wherein said removing water comprises removing water from said waste chemical in a plurality of discrete stages.

7. The chemical refining method as claimed in claim 1, wherein said removing particles comprises passing said waste chemical through a polyethylene filter.

8. A purification system for refining and reusing a chemical used in a semiconductor device fabrication process, the system comprising:

a processing part for using said chemical in an initial raw state and in a refined reusable state, wherein said chemical is Isopropyl Alcohol (IPA);

a waste tank for storing the chemical used in said processing part as waste chemical;

an ionic impurity removal part connected to said waste tank for removing ionic impurities from said waste chemical;

a metallic impurity removal part connected to said ionic impurity removal part for removing metallic impurities from said waste chemical;

a water removal part connected to a downstream end of said metallic impurity removal part for removing water from said waste chemical, after the metallic impurities are removed, until the percentage of water in the waste chemical is at the same level as that of the chemical in its initial raw state;

a particle removal part connected to said water removal part for removing particles from said waste chemical; and at least one storage tank, disposed downstream of said ionic impurity removal part, said metallic impurity removal part, said water removal part and said particle removal part, for storing said waste chemical which has passed through said particle removal part and for supplying said waste chemical to said processing part.

9. The purification system as claimed in claim 8, wherein said ionic impurity removal part comprises a charging material provided in a path through which said waste chemical travels to remove ions.

10. The purification system as claimed in claim 8, wherein said metallic impurity removal part comprises a heating device to heat and vaporize said waste chemical, and a collecting device to collect and cool the vaporized waste chemical.

11. The purification system as claimed in claim 8, wherein said water removal part comprises a heating device to heat and vaporize the waste chemical while in a vacuum state, a filter operative to allow water to pass therethrough while blocking passage of the vaporized waste chemical, and a collecting device to collect the vaporized waste chemical.

12. The purification system as claimed in claim 11, wherein said water removal part comprises a plurality of water removal devices connected in series.

13. The purification system as claimed in claim 8, wherein said particle removal part comprises a polyethylene filter.

14. The purification system as claimed in claim 8, wherein said at least one storage tank comprises a plurality of said storage tanks connected in parallel.

15. The purification system as claimed in claim 8, wherein said processing part is a bath into which wafers are dipped.

* * * * *